(12) United States Patent
Berci

(10) Patent No.: US 8,982,203 B2
(45) Date of Patent: Mar. 17, 2015

(54) VIDEO SYSTEM FOR VIEWING AN OBJECT ON A BODY

(75) Inventor: George Berci, Los Angeles, CA (US)

(73) Assignee: Karl Storz GmbH & Co. KG (DE)

( * ) Notice: Subject to any disclaimer, the term of this patent is extended or adjusted under 35 U.S.C. 154(b) by 1485 days.

(21) Appl. No.: 11/758,962

(22) Filed: Jun. 6, 2007

(65) Prior Publication Data

US 2008/0303899 A1 Dec. 11, 2008

(51) Int. Cl.
*A61B 1/04* (2006.01)
*A61B 1/00* (2006.01)
*A61B 1/055* (2006.01)
*A61B 19/00* (2006.01)

(52) U.S. Cl.
CPC .......... *A61B 1/00149* (2013.01); *A61B 1/00163* (2013.01); *A61B 1/00188* (2013.01); *A61B 1/055* (2013.01); *A61B 19/5212* (2013.01)
USPC .......................................... 348/74

(58) Field of Classification Search
USPC ................... 348/65–76, 42, 45; 600/101–183
See application file for complete search history.

(56) References Cited

U.S. PATENT DOCUMENTS

| | | | |
|---|---|---|---|
| 4,211,229 A | 7/1980 | Wurster | |
| 4,588,294 A | 5/1986 | Siegmund | |
| 4,740,058 A | 4/1988 | Hori et al. | |
| 4,987,488 A * | 1/1991 | Berci | 348/77 |
| 5,005,957 A | 4/1991 | Kanamori et al. | |
| 5,053,794 A * | 10/1991 | Benz | 396/432 |
| 5,059,009 A | 10/1991 | McKinley | |
| 5,416,634 A | 5/1995 | Ning | |
| 5,418,645 A | 5/1995 | Coath et al. | |
| 5,495,286 A | 2/1996 | Adair | |
| 5,496,261 A | 3/1996 | Sander | |
| 5,539,971 A * | 7/1996 | Kelly | 29/418 |
| 5,568,188 A | 10/1996 | Widmer et al. | |
| 5,579,772 A | 12/1996 | Kinukawa et al. | |
| 5,668,660 A | 9/1997 | Hunt | |

(Continued)

FOREIGN PATENT DOCUMENTS

| | | | |
|---|---|---|---|
| JP | 6030896 A | 2/1994 | |
| JP | 2001061776 A | 3/2001 | |

(Continued)

OTHER PUBLICATIONS

International Search Report, PCT/US08/07160, Sep. 26, 2008, 4 Pages.

(Continued)

*Primary Examiner* — Ruolei Zong
(74) *Attorney, Agent, or Firm* — St. Onge Steward Johnston & Reens LLC

(57) ABSTRACT

The present invention relates to a video system for viewing an object on a body, including an endoscopic lens for capturing an image, an endoscopic camera head attached to the endoscopic lens for transmitting the image, and a camera control unit attached to the endoscopic camera head for receiving the transmitted image. The endoscopic lens has a field of view, where the object is within the field of view. The endoscopic camera lens has a depth of field between approximately 10 mm and approximately 15 mm. The system also has an arm attached to the endoscopic lens for holding the endoscopic lens between approximately 180 mm and approximately 220 mm away from the surgical field. The magnified image is conveniently seen on large high definition screen.

21 Claims, 6 Drawing Sheets

(56) References Cited

U.S. PATENT DOCUMENTS

| | | | |
|---|---|---|---|
| 5,867,210 A | 2/1999 | Rod | |
| 5,889,611 A | 3/1999 | Zonneveld | |
| 6,190,308 B1 | 2/2001 | Irion et al. | |
| 6,318,864 B1 | 11/2001 | Fukaya et al. | |
| 6,400,514 B2 | 6/2002 | Minami et al. | |
| 6,466,432 B1 | 10/2002 | Beger | |
| 6,582,362 B2 | 6/2003 | Konno | |
| 6,640,131 B1 * | 10/2003 | Irion et al. | 600/476 |
| 7,126,303 B2 * | 10/2006 | Farritor et al. | 318/568.12 |
| 7,394,979 B2 * | 7/2008 | Luther et al. | 396/432 |
| 7,476,873 B2 * | 1/2009 | Hayashi | 250/458.1 |
| 7,539,410 B2 * | 5/2009 | Ishiyama | 396/287 |
| 7,594,188 B2 * | 9/2009 | Rudolph et al. | 715/810 |
| 7,704,206 B2 * | 4/2010 | Suzuki et al. | 600/178 |
| 7,910,868 B2 * | 3/2011 | Suzuki et al. | 250/201.2 |
| 2002/0027723 A1 | 3/2002 | Lei | |
| 2002/0080571 A1 | 6/2002 | Beger | |
| 2004/0036962 A1 | 2/2004 | Brunner et al. | |
| 2004/0125446 A1 | 7/2004 | Lei | |
| 2004/0156017 A1 | 8/2004 | Sander | |
| 2004/0263680 A1 | 12/2004 | Sonnenschein et al. | |
| 2005/0015005 A1 | 1/2005 | Kockro | |
| 2005/0057800 A1 | 3/2005 | Obrebski et al. | |
| 2005/0203374 A1 | 9/2005 | Vilsmeier | |
| 2005/0228257 A1 | 10/2005 | Ishikawa et al. | |
| 2005/0256371 A1 | 11/2005 | Schara et al. | |
| 2005/0267329 A1 | 12/2005 | Konstorum et al. | |
| 2006/0100497 A1 | 5/2006 | Sawazaki et al. | |
| 2006/0203330 A1 | 9/2006 | Moeller et al. | |
| 2006/0238857 A1 | 10/2006 | Sander | |

FOREIGN PATENT DOCUMENTS

| | | |
|---|---|---|
| JP | 2001 - 133696 | 5/2001 |
| JP | 2004147777 A | 5/2004 |
| JP | 2005110940 A | 4/2005 |
| JP | 2005118457 A | 5/2005 |
| JP | 2006255001 A | 9/2006 |
| JP | 2006305156 A | 11/2006 |
| JP | 2007133175 A | 5/2007 |
| SE | 52 04 01 | 7/2003 |

OTHER PUBLICATIONS

Writtin Opinion of the International Searching Authority, Sep. 26, 2008, 6 Pges.

Sekiya, et al.; "Development of a Dual-View Endoscope System"; Proc. SPIE 6080, 60800E (2006); pp. 1-10.

European Search Report; Application No. EP 08 76 8233; Issued: Oct. 5, 2011; 6 pages.

Olympus—Equipment Pour L'endoscopie; Item Nos. EQ-65 & EQ-60; May 2004; 4 pages.

Olympus—Systems Integration; Item Nos. INT-110, INT-135 & INT-320; Jan. 2009; 5 pages.

Olympus—Telescopes; Item Nos. TEL-310, TEL-335, TEL-230, TEL-145, TEL-140, TEL-125, TEL-116 and TEL-105; Dec. 2008; 13 pages.

* cited by examiner

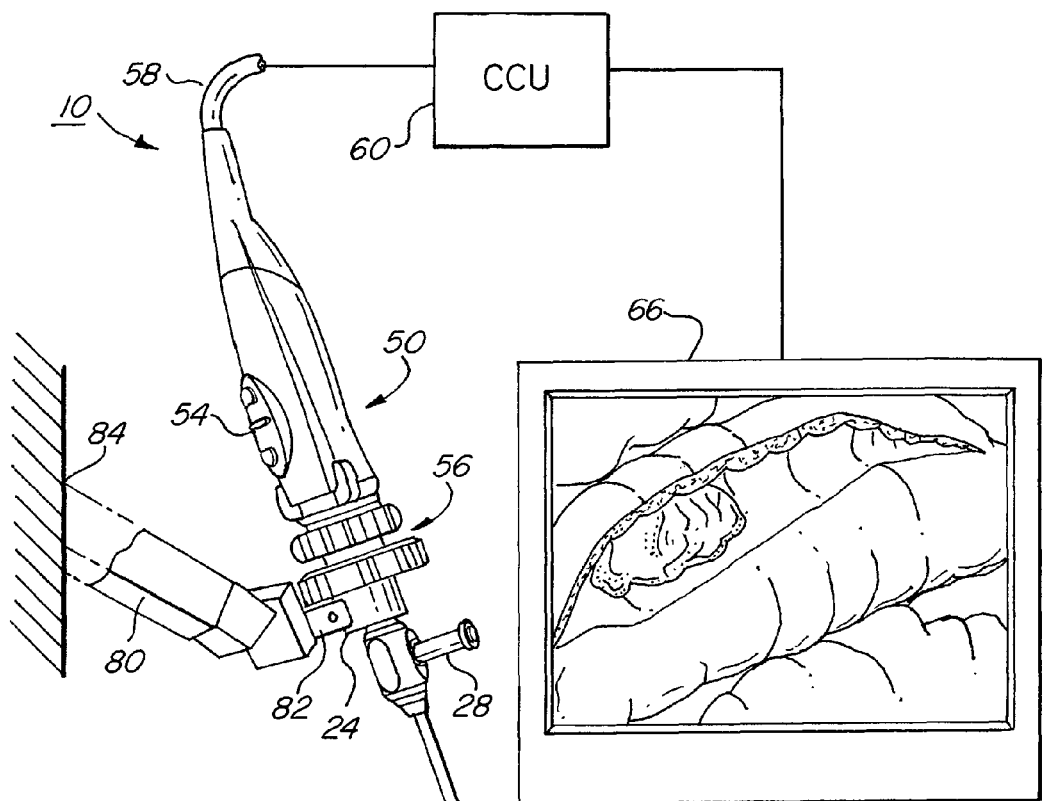
FIG. 2
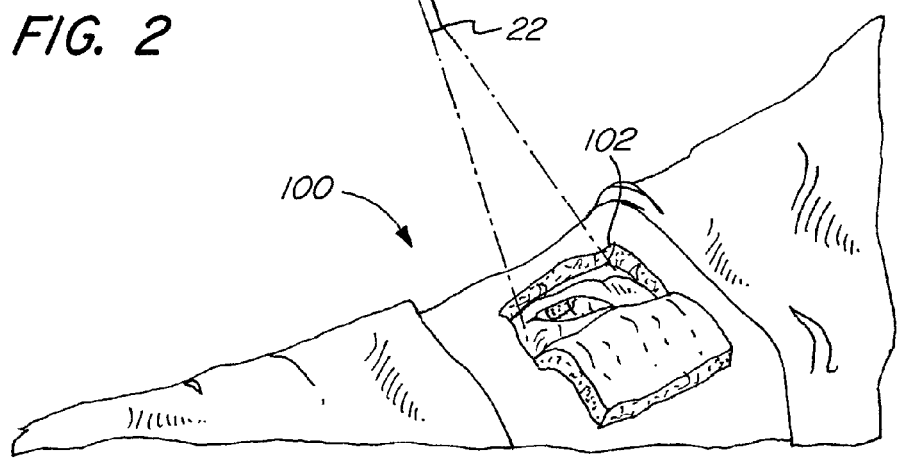

VIDEO SYSTEM FOR VIEWING AN OBJECT ON A BODY

FIELD OF THE INVENTION

The present invention relates to the field of microsurgery.

BACKGROUND OF THE INVENTION

Doctors and surgeons traditionally used optical systems to visualize surgical fields on and in the body. Although a surgeon may perform many procedures with the naked eye, a number of procedures often require magnified images of the surgical field for the surgeon to operate. It is known to magnify images of a surgical field to obtain a detailed view upon which the surgeon may reference while performing an operation or examination. Surgical procedures using image magnification techniques to view a surgical field are referred to as microsurgery. Microsurgery is commonly used in neurosurgery, including brain and spinal surgeries performed by neurosurgeons and orthopedic surgeons. Another use of microsurgery is anastomosis, or artificial connection, of blood vessels and nerves which are usually 1 mm in diameter or smaller. Further examples of microsurgery include procedures by otolaryngologists on the inner ear, and the vocal chords, and procedures by urologist and gynecologists to reverse vasectomies or tubal ligations.

The surgical microscope is a known device used to obtain magnified views of a surgical field visible from outside the body. The surgical microscope allows a surgeon to observe a magnified image of the surgical field visible from outside the body. Microscopes of this type use an optical lens system for receiving, magnifying, and displaying an optical image of the surgical field. The surgical microscope includes a monocular or binocular with relatively small pupils for viewing the images. Most surgical microscopes further include a second monocular or binocular and a means of splitting the optical beam to provide a surgeon's assistant with a means to view the image. Known surgical microscopes further include an optical globe or flexible light cable connected to an external light source for illuminating the surgical field visible from outside the body.

Although the surgical microscope allows a surgeon to observe magnified images of a surgical field visible from outside the body, the surgical microscope has many drawbacks and disadvantages.

A disadvantage of the surgical microscope is its relatively large size. The surgical microscope is a large device that must be supported over the surgical field on a stand adjacent to the operating table. The size of the surgical microscope limits the working space around the operating table. The microscope must further be cantilevered on its stand with a cumbersome counterbalance the microscope over the surgical field. Moreover, a dedicated assistant is required to operate the surgical microscope and maintain the surgical microscope, prior to, during, and after a surgery. Further, the surgical microscope is not part of the sterile field, and must be draped prior to use, and undraped after use thus increasing maintenance time, costs, and constraints on mobility.

Another disadvantage of the surgical microscope is that the surgeon and/or assistant must peer through binocular pupils to view the magnified images of the surgical field. Constantly looking into the pupils causes fatigue in the surgeon and assistant who use the microscope because they must maintain their eyes in close proximity of the viewing pupils for extended periods of time. This requirement also causes fatigue because the surgeon and assistant must lean over the operating table to look into the pupils, while at the same time performing the surgery below. As mentioned above, many surgical microscopes include multiple sets of binoculars to allow multiple users to simultaneously view magnified images of the surgical field. Multiple view ports reduce image intensity by factor equal to the number of binoculars, because a beam splitter is used to split the received optical image and direct it to each set of binoculars.

Another disadvantage of the surgical microscope is that is has an extremely shallow depth of field, approximately 1-2 mm. This limitation means that the microscope can only maintain a focus depth of about 1 mm in front of the focal point and a depth of about 1 mm past the focal point. 1-2 mm is not a sufficient depth of field to perform many microsurgical procedures without adjusting the focus during the procedure. To properly view the full surgical field the surgeon or her assistant must continually refocus the microscope to maintain the surgical field in focus.

Another disadvantage of the surgical microscope is that it requires a high intensity light source to provide images. The surgical microscope may either include an optical globe or flexible light source connected to an external source of illumination to produce the necessary light intensity. The light source increases the weight and size of the surgical microscope.

Another disadvantage of the surgical microscope is its cost. A new surgical microscope costs approximately between $230,000 and $250,000. Once purchased, the surgical microscope further requires a dedicated technician to operate, position, and maintain. The microscope additionally requires a very large storage area in or around the operating room. This is increasingly a disadvantage in today's operating rooms as the amount and size of surgical equipment continues to increase, while storage space in and around the operating room decreases.

One device that has been developed to overcome the disadvantages of the surgical microscope described above is U.S. Pat. No. 4,987,488 to Berci. The '488 patent discloses a video system for visualizing a surgical field with an enhanced depth of field. This disclosure relates to an improved system for viewing and magnifying images of the surgical field. The system uses a variable focal zoom lens connected to a high resolution video camera. The camera is further connected to a means of displaying images of the surgical field in the operating room such as a video monitor mounted above the operating table.

A possible disadvantage of the video system disclosed in the '488 patent is that a specific camera, namely a high resolution color video camera with a particular sensor area, is required. Therefore, interchanging another camera with the higher resolution camera disclosed in the '488 patent may not be possible.

In addition, camera control units ("CCU") are typically compatible with a limited number of camera heads. A CCU's hardware is usually difficult to configure for proper communication with varying types of camera heads because camera heads use varying types of imaging devices that can differ in pixel resolution, timing requirements (i.e. PAL, NTSC, Progressive, and other formats), signal output type (i.e. analog or digital), physical size, and in other characteristics. Since the CCU is typically compatible with a select number of camera heads, changing the camera head usually means the CCU needs to be changed as well, and vice versa.

A further disadvantage of the video system is that the hospital operating room staff must store and maintain the new lens and the new camera. This requirement further increases the cost of the video system. The hospital must develop and put into place procedures for maintaining the new equipment, and then train staff to follow those procedures. The hospital must further dedicate a storage area for the equipment in an already crowded operating room.

Another optical system for inspecting the body is endoscopy, where surgeons can view and operate on a surgical field not visible from outside the body, for example on the stomach of the uterus. An endoscope is typically a long slender device using fiber optics and powerful (ROD) lens systems to provide lighting and visualization of the interior of a body. A portion of the endoscope inserted into a small incision in the body to receive optical images of a surgical field not visible from outside the body.

Another disadvantage of the video system is that is does not utilize existing operating room equipment to visualize a surgical field from outside the body, but rather requires an additional expense for equipment dedicated to a single task.

In FIG. 1, a prior art video system for receiving images not visible from outside the body is shown. The system comprises a telescope lens connected to an endoscopic camera head. The distal end of the telescope lens is inserted into an incision in the body and receives images of surgical field not visible from outside the body. Generally, the distal, image receiving end, of the telescope lens is adjacent or in close proximity to the surgical field, and provides little magnification.

As a result of the increase in endoscopic procedures, many operating rooms are equipped with an assortment of equipment to perform such endoscopic procedures. For example, most hospitals already own one or more endoscopic camera heads for coupling with a telescope lens and receiving images not visible from outside the body. The endoscopic camera head is designed to detachably couple with endoscopic lenses to obtain images from inside the body. Another example of a widely used endoscopic tool is the camera control unit which connects to the endoscopic camera head. Camera control units are designed to work with specific camera heads. Hospitals that own one or more endoscopic camera head also own the associated camera control units for operating the camera control heads.

In general, all or most of a hospital's endoscopic cameras are compatible with all of the associated camera control units because manufactures of a specific brand strive to provide compatibility in their product lines. Hospitals tend to purchase a portion of their endoscopic equipment from one supplier or manufacturer as the surgeon's and administrators become comfortable with a brand. Therefore because one of a plurality of camera control heads is compatible with one of a plurality of camera control units, the there is a great deal of flexibility the use of surgical equipment. It is therefore desired to be able to use one of a plurality of camera heads to connect to a microsurgery lens, and connect the one of a plurality of camera heads to one of a plurality of camera control units.

Moreover, many operating rooms are increasingly equipped with high definition audio video equipment to interface with the endoscopic equipment. For example operating rooms designed for endoscopic procedures include high definition monitors for viewing the surgery. The operating rooms further include computer equipment for receiving, monitoring, and distributing signals obtained from the endoscopic equipment.

What is desired therefore is a procedure that permits viewing of an object in a field of view while overcoming the disadvantages of the surgical microscope and the '488 patent. Another desire is a procedure that permits viewing of the object in the field of view in a simplified manner.

SUMMARY OF THE INVENTION

Accordingly, it is an object of the present invention to provide a video system that is completely placed outside the body A further object of the present invention is to provide a video system which uses existing operating room equipment to receive, magnify, transmit, and display images of a surgical field.

Another object of the present invention is to provide a video system which can interface with existing operating room audio video equipment. For example the video system can interface with high definition displays, digital recording devices, and other existing audio video technology.

Another object of the present invention is to provide a video system comprising a camera and a lens wherein the camera and lens are autoclavable.

Another object of the present invention is to provide a video system comprising a camera and a lens wherein the camera and the lens are supported above the surgical field and the means of supporting the camera and the lens above the surgical field allows the surgeon to obtain images from a range of positions and angles during a surgical procedure.

Another object of the present invention is to provide a video system which can receive, magnify, and transmit images of a surgical field under standard operating room lights, without an additional lighting source dedicated solely to the field of view.

These and other objects of the present invention are achieved by a video system for viewing an object on a body, including an endoscopic lens for capturing an image, an endoscopic camera head attached to the endoscopic lens for transmitting the image, and a camera control unit attached to the endoscopic camera head for receiving the transmitted image. The endoscopic lens has a field of view, where the object is within the field of view and where the field of view has a depth of field between approximately 10 mm and approximately 15 mm. The system also has an arm attached to the endoscopic lens for holding the endoscopic lens between approximately 180 mm and approximately 220 mm away from the field of view.

In some embodiments, the arm is robotic. In other embodiments, the arm is adjustable. In further embodiments, the arm is programmable.

The video system is in communication with a display and wherein the display depicts an image transmitted from the endoscopic lens. Optionally, the endoscopic lens includes an objective lens, a viewing lens, a relay lens between the objective lens and viewing lens, a rod lens, and a spacer.

In another embodiment, a video system for viewing an object on a body includes a telescope lens for capturing an image, a plurality of camera heads each being attachable to the telescope lens, and a plurality of camera control units each being attachable to each of the plurality of camera heads. The system also includes an arm attached to the telescope lens for holding the telescope between approximately 180 mm and approximately 220 mm away from a field of view, and wherein a user selects one of the plurality of camera heads and one of the plurality of camera control units to be used with the telescope lens.

In some embodiments, the telescope lens is placed outside the body for capturing images from outside the body. In further embodiments, the telescope lens has a depth of field between approximately 10 mm and approximately 15 mm. In other embodiments, the telescope lens has a depth of field of approximately 12 mm. Optionally, the telescope lens further comprises a light guide fiber or attachable dual condenser lenses attached to an external light source via a light guide fiber cable.

In another aspect of the invention, a method of viewing an object on a body includes the steps of providing an endoscopic lens, connecting an endoscopic camera head to the endoscopic lens, viewing the object with the endoscopic lens from a distance of approximately 200 mm, focusing the endoscopic lens with a depth of field of approximately 12 mm, and transmitting the image to a camera control unit using the endoscopic camera head.

In some embodiments, the method positions the endoscopic lens and endoscopic camera head outside the body. In other embodiments, the method supports both the endoscopic lens and the endoscopic camera head with a mechanical arm.

A technician may use the camera control unit to adjust different parameters of the received images or the endoscopic camera head, and transfer the images to one or more destinations. It is possible to adjust the focus and zoom (magnification) of the endoscopic camera head using the camera control unit. The endoscopic camera head further may include buttons for controlling the endoscopic camera head zoom lens. It is preferred that the camera control unit transfer the images to high definition monitors in around the operating room to provide the surgeon, and/or his assistants with a means of viewing magnified images of the surgical field. The camera control unit may further transfer the images to an apparatus for recording the images. In some operating rooms, the received images may be transferred outside of the operating room and hospital to any location in the world. In some embodiments it is preferred that the camera control unit first transfers the images to a data hub, wherein the images can be directed to many different destinations.

The present invention achieves its many advantages over the prior art by using existing operating room equipment in a new manner to achieve a new result, using a new method and combination of equipment. Specifically, the video system uses endoscopic equipment, designed and built for receiving images of a surgical field not visible from outside the body, to receive images of a surgical field visible from outside the body. As mentioned above, many operating rooms are now equipped to perform endoscopic procedures wherein surgeons use endoscopes to perform minimally invasive surgeries by inserting endoscopes into small incisions in the body to view and operate on surgical fields not visible from outside the body.

This invention and its particular features and advantages will become more apparent from the following detailed description considered with reference to the accompanying drawings.

BRIEF DESCRIPTION OF THE DRAWING

FIG. 2 is a perspective view of the present invention.

DETAILED DESCRIPTION OF THE DRAWINGS

Figure 1:
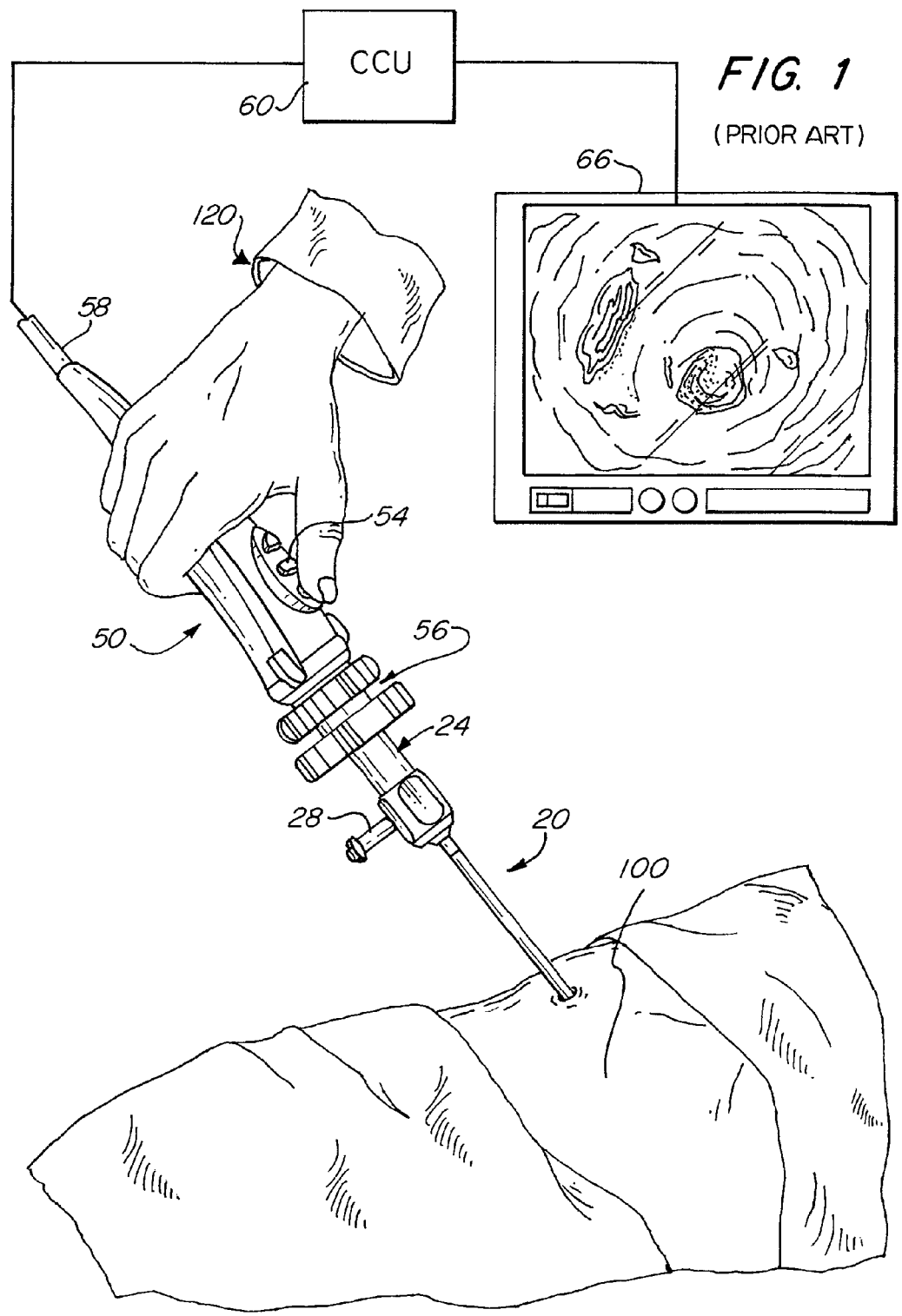
FIG. 1 is perspective view of the prior art use of an endoscopic camera head and telescope lens.

Referring to FIG. 2, one embodiment of video system in accordance with the present invention is shown. Video system 10 includes a telescope lens 20 with an endoscope eye piece 26. Video system 10 further includes an endoscopic camera head 50 optically connected to the endoscope eye piece 36 of the telescope lens 20, wherein the telescope lens 20 receives optical images visible from outside the body 100 and transmits optical images to endoscopic camera head 50. The endoscopic camera head 50 converts the optical images to digital images and transmits the images to camera control unit 60. Camera control unit 60 distributes and/or transmits received images to different points inside and/or outside the operating room 110. Camera control unit 60 controls different parameters of the endoscopic camera head 50, for example the camera control unit 60 controls a zoom function on the endoscopic camera head 50.

Referring to FIG. 2 a telescope lens 20 is shown. The telescope lens 20 is a long slender tube 21 with lenses disposed inside the tube 21 for receiving, affecting, and transmitting optical images. The telescope lens 20 has a distal end 22, also referred to an objective end, and a proximal end 24. One or more lenses are arranged inside the telescope lens 20 to receive, affect, and transmit optical images. In one embodiment of the present invention the distal end of the telescope 22 includes an objective lens 30 or objective lens assembly 30 for receiving, affecting, and transmitting optical images. The objective lens assembly 30 contains one or more moveable lens for affecting the received optical image, for example focusing the image, obtaining a wide angle view or zooming. In some embodiments the proximal end 24 of the telescope lens 20 also includes a viewing lens 48. It should be understood that many different type or lens arrangement are possible to achieve the desired receipt, transmission, and affect of optical images.

In general endoscopy the objective lens arrangement 30 may comprise multiple sets of lenses to receive optical images of a surgical field 102 in close proximity to the distal end 22 of the telescope lens 20. An object to be viewed is located within a field of view, where the field of view is synonymous with a surgical field 102. The distance between the surgical field 102 and the distal end 22 of the telescope lens 20 is referred to the working distance 70. Lenses or lens sets are arranged such that the object of interest located at the working distance 70 is in focus. Therefore it is preferable in general endoscopy to arrange the different sets of objective lenses 30 to focus at a very short working distance 70 because surgical field 102 is close proximity the distal end 22 of the telescope lens 20 when inserted inside of the body 100. In contrast, the objective lens sets 30 in the present invention are arranged in a manner such as to receive optical images of a surgical field 102 at a working distance 70 of approximately 200 mm from the distal end 22 of the telescope lens 22 because the entire telescope lens 20 is located outside the body 100. This working distance 70 gives the surgeon greater flexibility to move his hands or tools between the distal end 22 of the telescope lens 20 and the surgical field 102. It further allows the telescope lens to receive optical images with a wider field of view of the surgical field 102. In some embodiments, the working distance 70 is between approximately 180 mm and approximately 220 mm. In other embodiments, the working distance 70 is between approximately 150 mm and approximately 250 mm. In yet further embodiments, the working distance 70 is between approximately 100 mm and approximately 300 mm.

Figure 3:
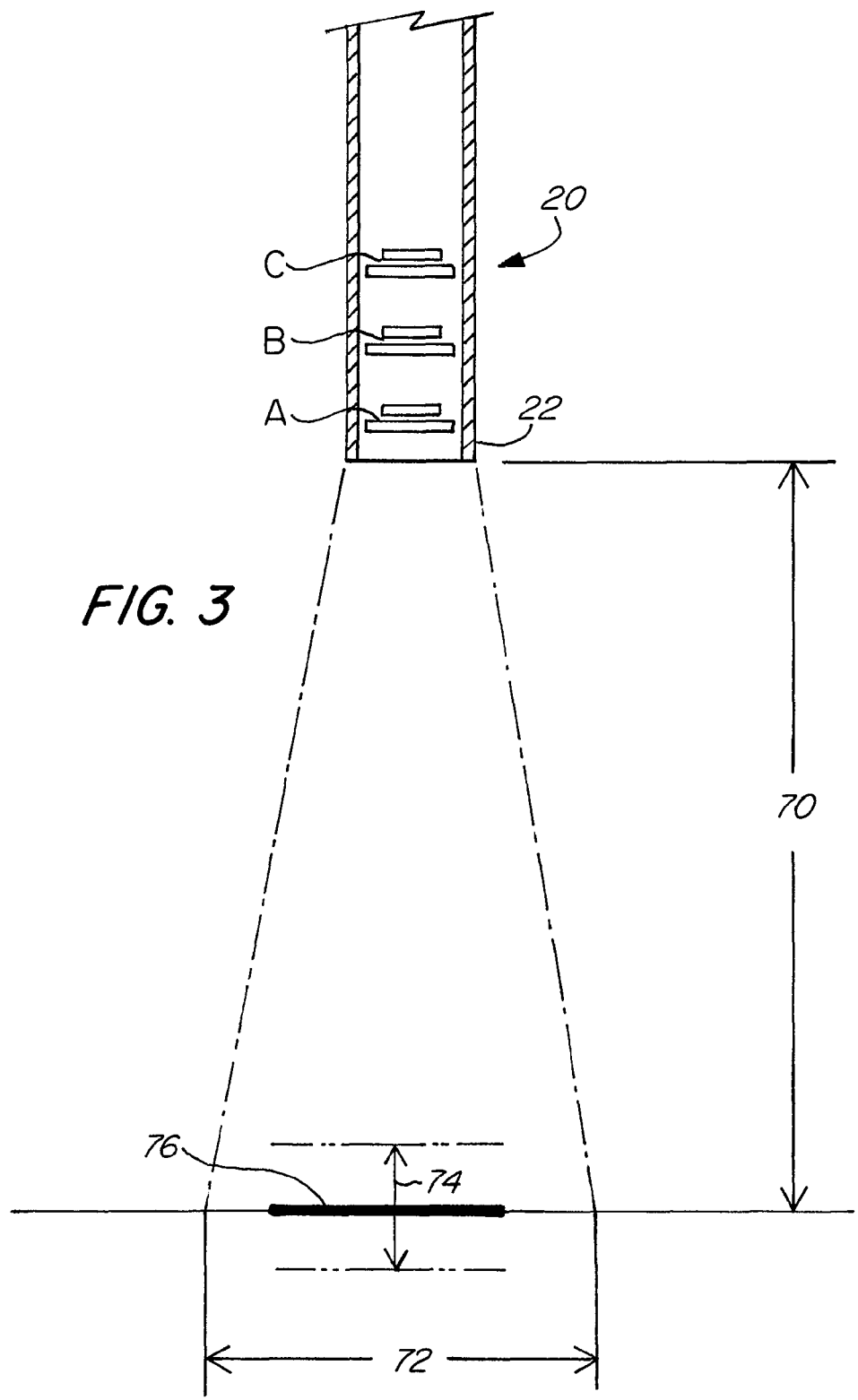
FIG. 3 is a side view of the telescope lens working distance shown in FIG. 1.
Figure 3A:
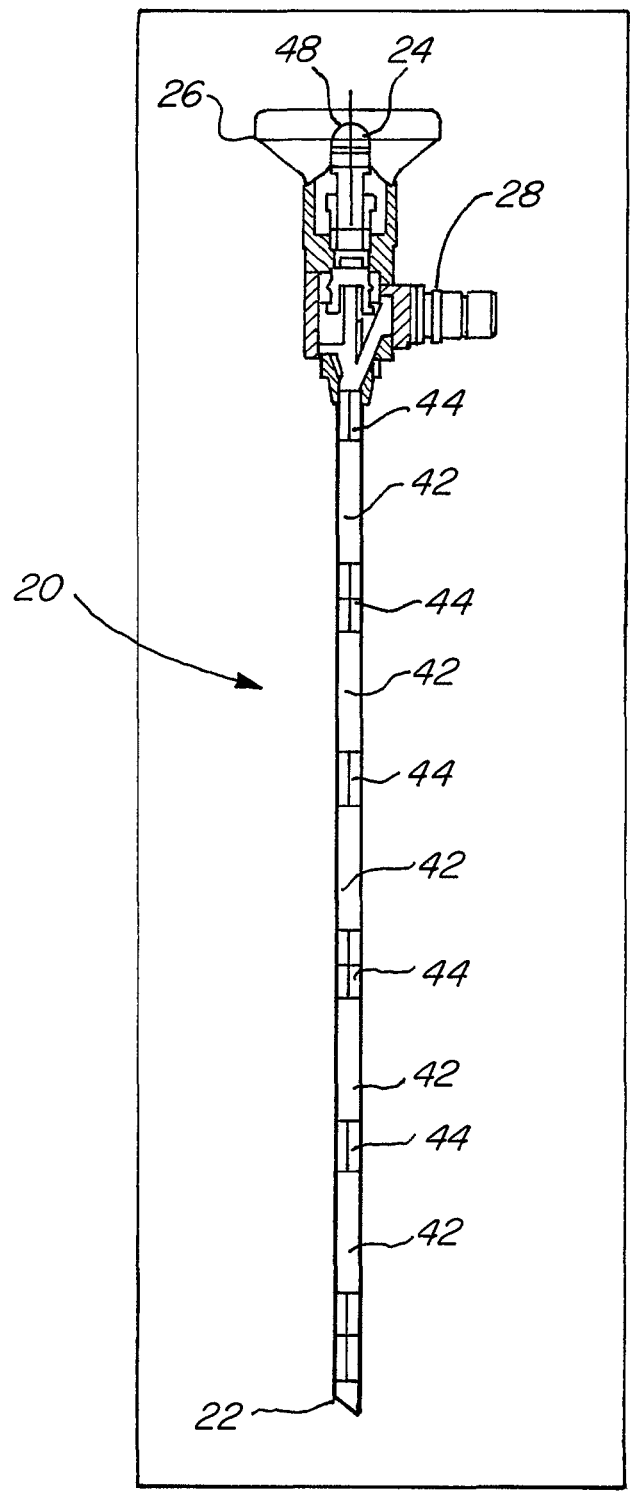
FIG. 3A is a side view of the inside of the telescope lens, wherein the objective lens arrangement is shown.

It is necessary to arrange the objective lens sets 30 to focus at a distance equal to the working distance 70. Referring to FIG. 3, the objective lens arrangement 30 comprises three sets of lens A 32, B 34 and C 36, wherein lens set A 32 is at the distal end 22 of the telescope lens 20 in the optical path between the surgical field 102 and the endoscopic camera head 50. Lens set B 34 is located in the optical path between lens set A 32 and the endoscopic camera head 50, and lens set C 36 is located in the optical path between lens set B 34 and the endoscopic camera head 50. If for example, the distance between lens set A 32 and lens set C 36 remains fixed, the effective working distance 70 of the lens arrangement 30, where an object is in focus, can be affected by changing the position of the middle lens set B 34. By locating lens set B 34 in close proximity to lens set C 36, the effective working distance 70 is reduced and objects close to the distal end 22 of the telescope lens 20 are in focus. On the other hand, by shifting lens set B 34 in close proximity to lens set A 32, the effective working distance 70 is increased and objects farther from the distal end 22 of the telescope lens 20 are in focus, as is preferred in the present invention. It should be understood that in some embodiments there are different lens arrangements including different sized and shaped lens, different numbers of lens sets, and spacing distances. Further, the lenses are constructed of different types of materials, which affect the refractive properties of the lenses. Each of these properties is interrelated, and provide for a multiple of possible arrangements to achieve the desired working distance 70 of approximately 200 mm.

In some embodiments of the present invention the telescope lens 20 further includes a relay lens 40 or lenses disposed inside the telescope lens in the optical path between the objective lens 30 or objective lens arrangement 30 and the viewing lens 48. The relay lens 40 transmits the optical image along the optical path the objective lens 30 and viewing lens 48 with minimal image distortion. The relay lens 40 comprises a series of rod lenses 42 and spacers 40 between the rod lenses 42. Many telescope lenses 20 used in endoscopy include relay lenses 40 because they allow for transmission of an optical image from a position inside a body 100 received at the distal end 22 of the telescope lens 20 to a position outside a body 100 at the proximal end 24 of the telescope lens 20 with minimal distortion to the optical image. The surgeon can insert the telescope lens 20 into the patient's body 100 to view a surgical field 102 not visible from outside the body 100 with minimal tissue damage, especially compared to previous surgical methods in which the patient's body 100 was fully opened to allow the surgeon to view the surgical field 102 not normally visible from outside the body 100.

The telescope lens 20 in the present invention is further provided with an eyepiece 26 at its proximal end 24. The eyepiece 26 is preferably of a standard size regardless of the diameter of the telescope lens 20. The eyepiece 26 connects the proximal end 24 of the telescope lens 20 to endoscopic camera head 50. The eyepiece 26 is detachably coupled to the endoscopic camera head 50 by a fastener, snap, or some other means known in the art. When the telescope lens 20 is detachably coupled to the endoscopic camera head 50 it transmits optical images received at its distal end 22 to a light receiving area 52 of the endoscopic camera head 50. The standard size of the endoscope eye piece 22 permits telescope lenses 20 of different diameters to readily connect to the same endoscopic camera head 50.

In the present invention it is preferred that the telescope lens 20 has an outside diameter of 10 mm, however it should be understood telescope lenses 20 are designed and manufactured in a range of diameters, and the present invention works with telescope lenses 20 having a range of different diameters and lengths. It is further preferred that the telescope lens 20 has a length of 100 mm as measured from its distal end 22 to proximal end 24, however it should be understood that telescope lenses 20 are designed and manufactured in a range of different lengths, and that the present invention works with telescope lenses 20 having a range of different lengths and sizes.

Further referring to FIG. 2, in some embodiments of the present invention the telescope lens 20 has a light port 28 for introducing a light source into the telescope lens 20. It is preferred that the telescope lens 20 includes light guide fibers for transmitting the light source from the light port 28 to the distal end 22 of the telescope lens 20. It should room source to receive images of a surgical field 102 visible from outside the body 100. It should further be understood that some embodiments of the telescope lens 20 do not include a light port 28 or light guide fibers or attachable dual condenser lenses attached to an external light source via a light guide fiber cable. For example, in some embodiments general operating room lights can also provide sufficient lighting for transmittal of optical images. It should be understood that some embodiments of the present invention require an external light source. It should be understood that in some embodiments of the present invention the lens telescope 20 contains channels in addition to the channel for relaying the received images. For example, the telescope lens 20 includes a channel for irrigation, or a channel for inserting instruments into the body 100.

The distance between the distal end 22 of the telescope lens 20 and the surgical field 102 is referred to as the working distance 70. During an endoscopic surgical procedure the distal end 22 of the telescope lens 20 is inserted into a patient's body 100 and receives and transmits optical images of a surgical field 102 not visible from outside the body 100 to the proximal end 24 of the telescope lens 20 located outside the body 100. The lenses disposed within the telescope lens 20, specifically the objective lens 30, or objective lens arrangement 30, are arranged to have a relatively short working distance 70 because the surgical field 102 is relatively close to the distal end 22 of the telescope lens 20. For instance, during an endoscopic surgical procedure the surgical field 102 is located less than 1 cm from the distal end 22 of the telescope 20.

In the present invention, however, the entire telescope lens 20 is located outside of the body 100. Further the purpose of the video system 10 is to receive images of a surgical field 102 visible from outside the body 100, and to magnify the images and transmit the images, providing the surgeon with a detailed reference of the surgical field 102. It is preferred that the working distance 70 of the present invention is approximately 200 mm. This distance allows for sufficient distance between the distal end of the telescope 22 and the surgical field 102 for the surgeon to manipulate his hands and tools. It further provides a sufficient field of view of the surgical field 102.

It is preferred that the depth of field 74 of the present invention is approximately 12 mm, 6 mm in front of the focal point 76 and 6 mm past the focal point 76. The depth of field 74 refers to the distance in front of the focal point 76 and behind the focal point 76, which appears in focus without adjusting the lenses or the working distance 70. At the working distance 70 of 200 mm it is preferred that the depth of field 74 is approximately 12 mm, or 6 mm in front of the focal point 76 and 6 mm past the focal point 76. A large depth of field 74 is preferred because it allows the surgeon to view the entire surgical field 102 without adjustments of the working distance 70. For example with a shallow depth of field 74 only 2 or 3 mm are in focus. As a result the surgeon, or his assistant, must constantly refocus the microscope to maintain the surgical field 102 in focus. However, with a larger depth of field 74, such as with the present invention, the entire surgical field 102 remains focus, and there is no need for tedious adjustments of the focus. In some embodiments, depth of field 74 is between approximately 10 mm and approximately 15 mm. In other embodiments the depth of field 74 is between approximately 8 mm and approximately 20 mm. It should be understood that many different lens arrangements and parameters may be used with the present invention.

As discussed above, the telescope lens 20 receives optical images at its distal end 22 and transmits the images to its proximal end 24. It should be understood that it is possible to manipulate the lenses to affect the angle upon which the distal end 22 of the telescope lens 20 receives optical images. For example, in some embodiments the telescope lens 20 is arranged to receive optical images from directly in front of its distal end 22 or in the alternative, in other embodiments telescope lens 20 is arranged so that the distal end 22 receives optical images at an angle. It should be further understood that in some embodiments the telescope lens 20 has variable focus lenses, wherein the lenses can by focused on focal points at varying distances from the distal end 22 of the telescope lens 20.

Figure 4:
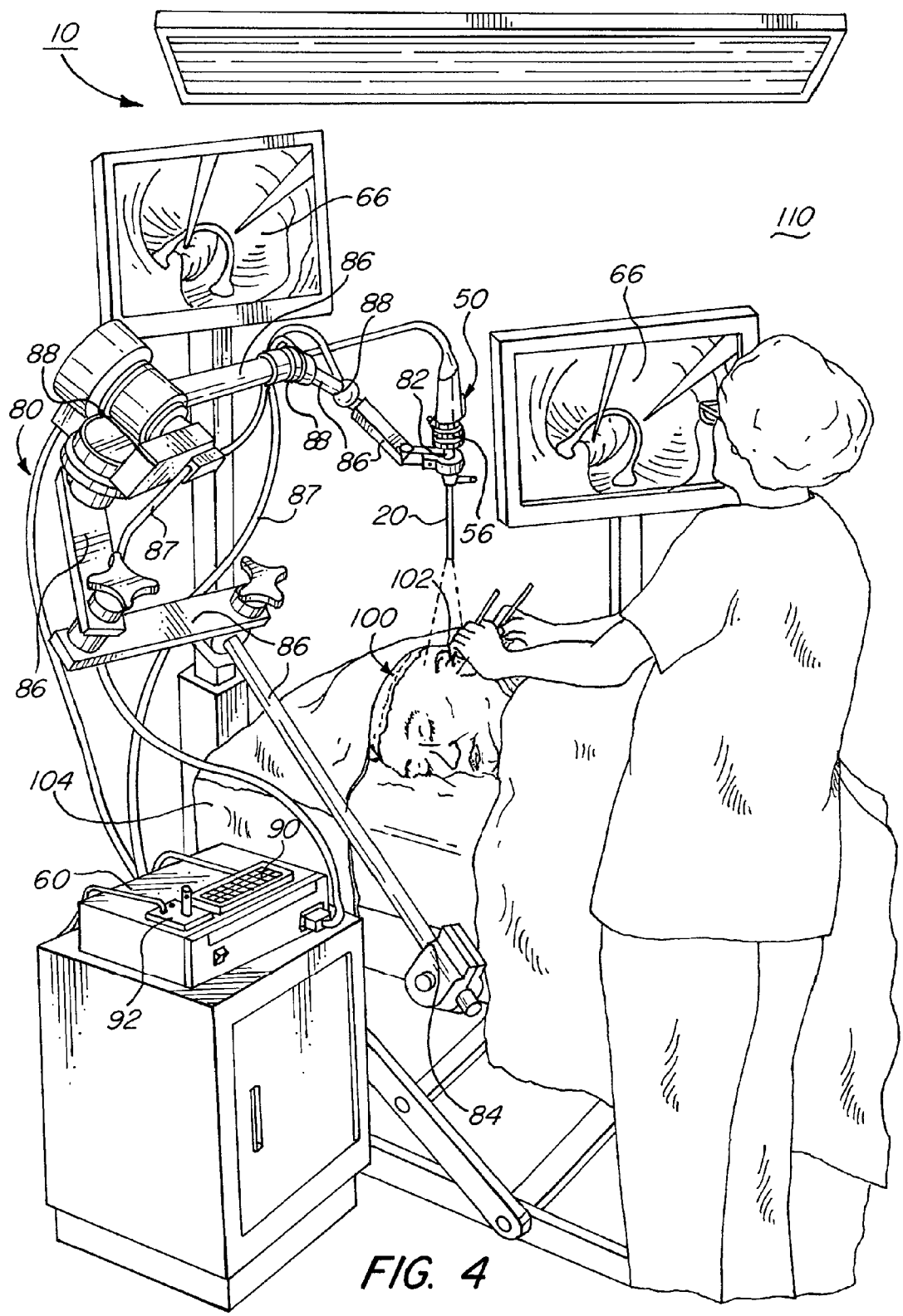
FIG. 4 is a perspective view of the invention shown in FIG. 1 in use during a microsurgical procedure.

In FIGS. 2 and 4 an endoscopic camera head 50 in accordance with the present invention is shown. An endoscopic camera head 50 is a camera head for receiving optical images wherein the endoscopic camera head 50 is specifically designed to receive optical images from an endoscopic instrument inserted into a body, for example an telescope lens 20. Specifically the endoscopic camera head 50 includes a standard optical coupling 56 for detachably coupling to an eye piece 26 of an endoscopic instrument, for example a telescope lens 20. The eye piece 26 of the telescope lens 20 is detachably coupled to the standard optical coupling 56 endoscopic camera head 50. In some embodiments the optical coupling 56 is a cup with in inside diameter slightly larger that that of the telescope lens eyepiece 26. The cup accepts the eye piece 26 in the form of a male female connection. In some embodiments the coupling further includes screws or a cap to secure the telescope eye piece 26 in place and facilitate the transmission of optical images from the telescope lens 20 to the endoscopic camera head 50. It is preferable that the standard optical coupling 56 is designed to accept a wide range of endoscopic instruments.

An example of an endoscopic camera head 50 is the Image 1™ manufactured by Karl Storz. Referring to FIG. 2 an embodiment of an endoscopic camera head 50, the Image 1™, is shown. The endoscopic camera head 50 includes a optical receiving area 52 for receiving optical images from the telescope lens 20. The optical receiving area 52 is located in the center of the standard optical coupling 56 to allow the optical image to pass to the endoscopic camera head 50. The endoscopic camera head 50 further includes a CCD sensing chip for receiving the optical image and converting it to a digital signal. The endoscopic camera head 50 further includes a standard optical coupling 56 for detachably coupling the telescope lens 20 or some other instrument to the endoscopic camera head 50. It should be understood that many types of endoscopic cameras heads 50 may be used with the present invention.

The Image 1™ endoscopic camera head 50 further includes a parafocal zoom lens located between the optical image receiving area 52 and the CCD sensing chip. The endoscopic camera head 50 includes programmable buttons 54 on its side for controlling different parameters of the endoscopic camera head 50. For example, the buttons can control the zoom of the endoscopic camera head 50.

Further the endoscopic camera head 50 shown is fully autoclavable and is placed in the sterile field during surgery. Furthermore, the telescope lens 20 described above is also fully autoclavable. This is beneficial because both the endoscopic camera head 50 and the telescope lens 20 are placed in the sterile field and touched by the surgeon during a surgical procedure. It should be understood that it is not necessary for the endoscopic camera head 50 or the telescope lens 20 to be autoclavable. In some embodiments of the present invention the endoscopic camera head 50 is a high definition camera head to provide the best picture quality Referring to FIG. 2, the endoscopic camera head 50 is electronically connected to a camera control unit 60. In some embodiments the connection is a wire, in other embodiments the connection is wireless. It is further preferred that the electronic connection provides power to the endoscopic camera head 50. The camera control unit 60 includes a means of processing the digital signal received from the endoscopic camera head 50, and distributing the digital signal to different equipment inside and outside the operating room 110. For example in some embodiments of the present invention the camera control unit 60 transmits the digital signals to a receiving unit inside the operating room, wherein the receiving unit acts as a hub for distributing the digital signals to different equipment. In other embodiments, camera control unit 60 is housed inside the endoscopic camera 20.

As mentioned above, the camera control unit 60 sends the digital signal to different receivers. It is preferable that digital image signal be sent to high definition televisions 66 located in the operating room 110 so that the surgeon can view images of the surgical field 102, while performing a surgery. It is preferred that the endoscopic camera head 50 receives and transmits digital images such as to produce a video of the surgical field 102. The digital signal may also be sent to a recording device, other hospitals, or a classroom.

As shown in FIG. 4, the endoscopic camera head 50 is connected to the camera control unit 60. The camera control unit 60 is connected to a display screen 66 that is mounted in the operating room for surgeon reference. In FIG. 4 the display screen 66 is mounted above the operating table on a stand enabling the surgeon and a surgical team to have a clear line of view to the display screen 66. The camera control unit 60 sends a digital signal to the display screen 66, and the display screen displays the images of the surgical field received by the endoscopic camera head 50. The display screen 66 is advantageous because it allows the surgeon to reference the display of the surgical field without looking into a set of binoculars or binocular eyepiece. The display screen 66 thus reduces surgeon fatigue. In some embodiments of the present invention, as shown in FIG. 4, there are multiple display screens 66 to allow for multiple positions from which the screen can be viewed. In some embodiments the display screen 66 is mounted on the ceiling of the operating room either directly or with a boom. In other embodiments the display screen is placed directly on the patient during the surgery. In some embodiments of the present invention the display screens 66 are high definition, high resolution monitors. In some embodiments of the present invention the camera control unit is connected to a data routing system wherein the digital output signal is routed to different points inside and outside the operating room.

Referring to FIGS. 2 and 4 the endoscopic camera head 50 and telescope lens 20 are located outside the body. The distal end 22 of the telescope lens 20 receives images of a surgical field 102 visible from outside the body 100 and transmits the optical images to the camera control unit 60. The endoscopic camera head 50 and telescope lens are supported in position to receive images of the surgical field 102 by a mechanical arm 80. It is preferable that the mechanical arm 80 is pneumatically controlled and/or magnetically controlled. The mechanical arm 80 allows the surgeon or assistant to position the distal end 22 telescope lens 20 directly above the surgical field 102. The mechanical arm 80 further allows the surgeon or her assistant to adjust the position of the endoscopic camera head 50 and telescope lens 20 to obtain the desired angle for viewing the surgical field 102. The magnetic and or pneumatic controls allow for precise control of the endoscopic camera head 50 position. It should be understood that in some embodiments one or more of the endoscopic camera head 50 and telescope lens 20 are supported by a stand next to the operating table, in other embodiments by a support boom connected to the ceiling, and finally in other embodiments by a surgeon or an assistant's hand, or other means.

Referring to FIG. 4, a robotically controlled mechanical arm 80 with multiple degrees of freedom is shown. The robotic mechanical arm 80 has a distal end 82 and a proximal end 84. The arm further comprises two or more rigid link members 86 connected with ball joints 88, hinges, or some other known means. The proximal end 84 of the arm is connected to the table 104, and the distal end 82 of the arm is connected to one or more of the telescope lens 20 and the endoscopic camera head 50 to support the combination above the surgical field 102. In some embodiments, the arm 80 is controlled by pneumatics, magnetics, or some other means to provide precise control of the location of the distal end of the arm.

The control elements 87 of the arm are connected to a control source 89, for example either a pressurized air source or source of electricity. The control elements 87 are used to maintain the mechanical arm 80 in a steady position or change the position of the arm. The control sources 87 are further connected to a processor and input means, such as keyboard 90 or joystick 92 to enable an operator to actuate the control elements 87 and change the position of the endoscopic camera head 50 and telescope lens 20 in relation to the surgical field 102. It is further possible to program the processor to run a predefined routine during a surgical procedure. For example, prior to a surgery a user programs a predefined control sequence into the processor using the keyboard 90 or processor. The control sequence defines specified parameters for controlling the arm 80 during the surgery. In some embodiments the arm remains in one position, and will move to a second predefined position upon the surgeons command. The program is stored it can be used in one or more surgeries. It should be understood that many other mechanical arm designs are possible and within the scope of the invention.

In one embodiment of the present invention the endoscopic camera head 50 and telescope lens 20 are supported and controlled above the operating table 104 using a Mitaka Company pneumo-magnetic mechanical arm 80. The mechanical control arm 80 allows for precise control of the position of the distal end 22 of the telescope lens 20. It is preferable that the Mitaka arm has multiple degrees of freedom to move the distal end 22 of the telescope lens 20 to different positions above the surgical field 102. For example, the surgeon or a technician programs the angle of the telescope lens 20 in relation to the surgical field 102 so that the endoscopic camera head 50 receives different optical images of the surgical field 102.

Figure 5:
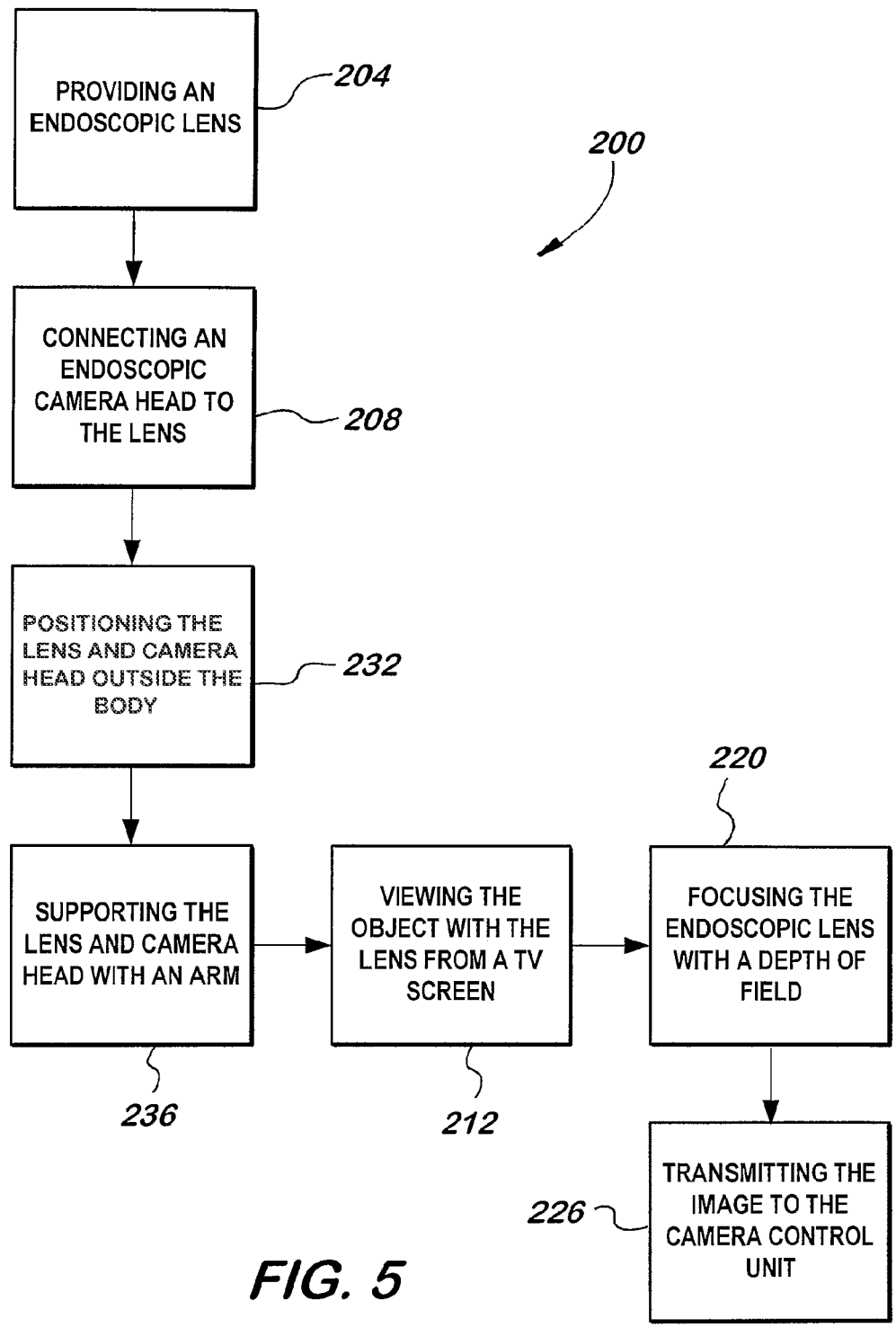
FIG. 5 depicts a method for providing the video system shown in FIG. 1.

FIG. 5 depicts method 200 for viewing an object on a body, including the steps of providing 204 an endoscopic lens, connecting 208 an endoscopic camera head to the endoscopic lens, viewing 212 the object with the endoscopic lens from a distance of approximately 200 mm, focusing 220 the endoscopic lens with a depth of field of approximately 12 mm, and transmitting 226 the image to a camera control unit using the endoscopic camera head.

In some embodiments, method 200 positions 232 the endoscopic lens and endoscopic camera head outside the body. In other embodiments, method 200 supports 236 both the endoscopic lens and the endoscopic camera head with the mechanical arm.

Although the invention has been described with reference to a particular arrangement of parts, features and the like, these are not intended to exhaust all possible arrangement or features, and indeed many other modifications and variations will be ascertainable to those of skill in the art.

What is claimed is:

1. A video system for viewing an object on a body, comprising:
    an elongated tube having an endoscopic lens positioned therein for capturing an image and an eyepiece located at a proximal end of said elongated tube, said eyepiece transmitting the image therethrough;
    an endoscopic camera head attachable to said eyepiece for receiving the image and generating an image signal;
    a camera control unit attached to said endoscopic camera head for receiving the image signal;
    said endoscopic lens has a field of view;
    said field of view has a depth of field ranging from 8 mm to 20 mm;
    an arm attached to said endoscopic lens for holding said endoscopic lens at a distance from said object ranging from 100 mm to 300 mm away from said object; and
    a light port positioned on said elongated tube and light guide fibers coupled to the light port for transmitting illuminating light from the light port to a distal end of said elongated tube.

2. The video system according to claim 1, wherein said arm is a robotic arm.

3. The video system according to claim 1, wherein said arm is adjustable.

4. The video system according to claim 1, wherein said arm is programmable.

5. The video system according to claim 1, wherein said camera control unit is in communication with a display and wherein said display depicts an image transmitted from said endoscopic lens.

6. The video system according to claim 1, wherein said endoscopic lens includes an objective lens, a viewing lens, a relay lens between the objective lens and viewing lens, a rod lens, and a spacer.

7. The video system of claim 1, wherein the endoscopic lens is a telescope lens.

8. The video system of claim 1, further comprising an external light source for illuminating an object.

9. The video system of claim 1, wherein said field of view has a depth of field ranging from 10 mm to 15 mm.

10. A video system for viewing an object on a body, comprising:
    an elongated tube having telescope lens positioned therein and an eyepiece located at a proximal end of said elongated tube, said eyepiece transmitting the image therethrough;
    a plurality of camera heads, each being attachable to said eyepiece;
    a plurality of camera control units, each being attachable to each of said plurality of camera heads;
    an arm attached to said telescope lens for holding said telescope at a distance from said object ranging from 100 mm to 300 mm away from the object; and a light port positioned on said elongated tube and light guide fibers coupled to the light port for transmitting illuminating light from the light port to a distal end of said elongated tube.

11. The video system according to claim 10, wherein said telescope lens has a depth of field between 10 mm and 15 mm.

12. The video system according to claim 10, wherein said telescope lens has a depth of field of 12 mm.

13. The video system according to claim 10, wherein said telescope lens further comprises a light guide fiber or attachable light source.

14. The video system according to claim 10, further comprising an external light source for illuminating an object.

15. The video system according to claim 10, wherein said telescope lens comprises one or more adjustable lenses to affect an angle upon which said telescope lens receives optical images.

16. The video system of claim 10, wherein said telescope lens has a depth of field ranging from 8 mm to 20 mm.

17. A method of viewing an object, comprising the steps of:
providing an elongated tube having endoscopic lens positioned therein and an eyepiece located at a proximal end of said elongated tube;
connecting an endoscopic camera head to the eyepiece;
providing a light port positioned on the elongated tube and coupling light guide fibers to the light port;
transmitting illuminating light from the light port to a distal end of the elongated tube;
viewing the object with the endoscopic lens from a distance of 100 mm to 300 mm from the object;
focusing the endoscopic lens with a depth of field ranging from 8 mm to 20 mm; and
transmitting the image to a camera control unit using the endoscopic camera head.

18. The method of claim 17, further comprising the step of supporting the endoscopic lens and said endoscopic camera head with a mechanical arm.

19. The method of claim 17, further comprising the step of presenting a magnified image on a display screen.

20. The method of claim 17, wherein said endoscopic lens is a telescope lens.

21. The method of claim 17, wherein the depth of field ranges from 10 mm to 15 mm.

* * * * *